United States Patent [19]

Uffenheimer

[11] Patent Number: 4,799,393

[45] Date of Patent: Jan. 24, 1989

[54] COMBINED CLOSED AND OPEN TUBE SAMPLING APPARATUS AND METHOD

[75] Inventor: Kenneth F. Uffenheimer, Chappaqua, N.Y.

[73] Assignee: Technicon Instruments Corporation, Tarrytown, N.Y.

[21] Appl. No.: 124,352

[22] Filed: Nov. 20, 1987

Related U.S. Application Data

[63] Continuation-in-part of Ser. No. 771,895, Sep. 3, 1985, abandoned.

[51] Int. Cl.$^4$ .............................................. B01L 3/02
[52] U.S. Cl. ................................................. 73/864.22
[58] Field of Search ............... 73/864, 864.21–864.25, 73/864.81, 864.83, 864.86, 863.01, 863.21–863.24, 864.85, 864.22; 422/100, 68, 81, 82, 89

[56] References Cited

U.S. PATENT DOCUMENTS

| | | | |
|---|---|---|---|
| 3,255,575 | 6/1966 | Roberts | 73/863.21 |
| 3,581,574 | 6/1971 | Smith | 73/864.23 |
| 3,672,226 | 6/1972 | Reid | 73/864.86 |
| 3,719,086 | 3/1973 | Bannister et al. | 73/864.22 |
| 3,748,911 | 7/1973 | Rousselet et al. | 73/864.22 |
| 3,795,149 | 3/1974 | Gillett et al. | 73/864.24 |
| 3,872,730 | 3/1975 | Ringrose et al. | 73/864.23 |
| 3,918,913 | 11/1975 | Stevenson et al. | 73/864.24 |
| 3,960,020 | 6/1976 | Gordon et al. | 73/864.22 |
| 3,991,055 | 11/1976 | Godin et al. | 73/864.84 |
| 4,108,602 | 8/1978 | Hanson et al. | 73/864.22 |
| 4,120,662 | 10/1978 | Fosslien | 73/864.24 |
| 4,152,391 | 5/1979 | Cabrera | 73/864.83 |
| 4,300,393 | 11/1981 | Stearns | 73/864.81 |
| 4,476,734 | 10/1984 | Banks et al. | 73/864.85 |
| 4,478,095 | 10/1984 | Bradley et al. | 73/864.21 |
| 4,512,203 | 4/1985 | Calone-Lonjean et al. | 73/863.81 |
| 4,512,953 | 4/1985 | Marsoner et al. | 422/81 |
| 4,516,437 | 5/1985 | Pedroso et al. | 73/864.22 |
| 4,520,108 | 5/1985 | Yoshida et al. | 73/864.81 |

FOREIGN PATENT DOCUMENTS

| | | | |
|---|---|---|---|
| 2547843 | 4/1977 | Fed. Rep. of Germany | 73/864.22 |
| 2075672 | 11/1981 | United Kingdom | 73/864.22 |

*Primary Examiner*—John Chapman
*Assistant Examiner*—Robert R. Raevis
*Attorney, Agent, or Firm*—Jeffrey M. Greenman; James J. Romano, Jr.

[57] ABSTRACT

Sampler apparatus and method are provided and include both closed and open tube samplers, and selector valve operable to select therebetween for sample supply to automated sample analysis apparatus. A shear valve divides the samples into separate sample quantities for independent sample quantity analysis by multi-channel sample analysis apparatus. A pressure equilibration chamber prevents vacuum build-up in the closed tube sampler to insure the supply of consistent sample quantities therefrom. A source of a pressurized rinse solution is provided; and is operatively connected to the sampler apparatus in such manner as to insure the particularly thorough rinsing and cleansing of all relevant sampler components to remove sample residue therefrom between sampling operations, thereby reducing sample carryover to levels below those of clinical significance.

17 Claims, 6 Drawing Sheets

COMBINED CLOSED AND OPEN TUBE SAMPLING APPARATUS AND METHOD

This application is a continuation-in-part of application Ser. No. 06/771,895, filed Sept. 3, 1985, and now abandoned.

BACKGROUND OF THE INVENTION

1. Field of the Invention.

This invention relates to new and improved sampling apparatus and method which are capable of automated sampling from both closed and open sample tubes attendant sample analysis.

2. Description of the Prior Art.

Although a number of closed tube samplers are known in the prior art, most relevantly in this instance the closed tube sampler included in the hematology instrument as marketed by Coulter Electronics, Inc., Hialeah, Fla. as the Coulter "S-PLUS VI," and the closed tube sampler included in the hematology instrument as marketed by Cortex Research Corporation, Northbrook, Ill. under the Trademark "Double Helix;" it may be understood that neither of these prior art closed tube samplers is configured or operable in the manner of the novel sampler of this invention to provide for versatility of application in terms of the immediately available option of automatically switching between closed and open tube sampling through use of simple selector valve means and essentially the same sample supply means without requirement for external modification in sampler configuration; to provide for simplicity of configuration and operation in terms of utilizing essentially the same flow paths for sample supply and for inter-sample sampler rinsing; or to provide for significantly increased sample analysis accuracy in terms of insuring the consistent supply of precisely determined and readily reproducible sample volumes attendant repeated sampling from the same closed sample tube, and in terms of the absolute minimization of sample carryover to levels below those of clinical significance.

Too, and although a particularly wide variety of open tube samplers are known in the prior art, most relevantly in this instance the open tube samplers as disclosed in U.S. Pat. Nos. 3,719,086, 3,756,459, 3,759,667, 3,912,452 and 4,065,973, it may be understood that none of these prior art open tube samplers is configured or operable in the manner of the novel sampler of this invention to provide for versatility of application in terms of the immediately available option of switching from open to closed tube sampling; to provide for simplicity of configuration in terms of utilizing essentially the same flow paths for sample supply and for inter-sample sampler rinsing; or to provide for significantly increased sample analysis accuracy in terms of the absolute minimization of sample carryover to levels below those of clinical significance for both open and closed tube sampling.

OBJECTS OF THE INVENTION

It is, accordingly, an object of this invention to provide new and improved sampler apparatus and method which are capable of automated sampling from both closed sample tubes and open sample tubes without external modification in sampler configuration.

Another object of this invention is the provision of new and improved sampler apparatus and method as above which are of relatively simple configuration and manners of operation.

Another object of this invention is the provision of new and improved sampler apparatus and method as above which are operable to insure the supply of consistent and readily reproducible sample volumes attendant closed tube sampling, thereby maximizing the accuracy of sample analysis results.

Another object of this invention is provision of new and improved sampler apparatus and method as above which are operable to minimize sample carryover levels below those of clinical significance, thereby further maximizing the accuracy of sample analysis results.

Another object of this invention is the provision of new and improved sample analysis apparatus and method.

A further object of this invention is the provision of new and improved sampler apparatus and method which are particularly adapted for use in automated hematology instruments.

SUMMARY OF THE INVENTION

As disclosed herein, the new and improved sampler apparatus and method of my invention comprise a closed tube sampler, an open tube sampler, sample supply means operatively associated therewith and operable to supply samples therefrom to automated sample analysis apparatus, and selector valve means operatively associated with the closed and open tube samplers, and the sample supply means, and operable to enable selection between the closed ane open tube samplers for sample supply to the analysis apparatus. Shear valve means operate to divide the thusly supplied samples into separate sample quantities for concomitant, independent sample quantity analysis by multi-channel sample analysis apparatus. The sample supply means include pressure equalization means which are operable upon closed tube sampler selection and operation to prevent vacuum build-up in the same, thereby insuring consistent sample quantity supply from the closed tube sampler with attendent maximization of the accuracy of the sample analysis results. Rinse means are operatively associated with the closed and open tube samplers, the sample supply means, the selector valve means, and the shear valve means, and are operable to particularly thoroughly rinse and cleanse the same of sample residue between sampling operations, thereby reducing sample carryover to levels below those of clinical significance and further maximizing the accuracy of the sample analysis results.

DESCRIPTION OF THE DRAWINGS

The above and other significant objects and advantages of my invention are believed made clear by the following detailed description thereof taken in conjunction with the accompanying drawings wherein.

DETAILED DESCRIPTION OF THE INVENTION

Figure 1:
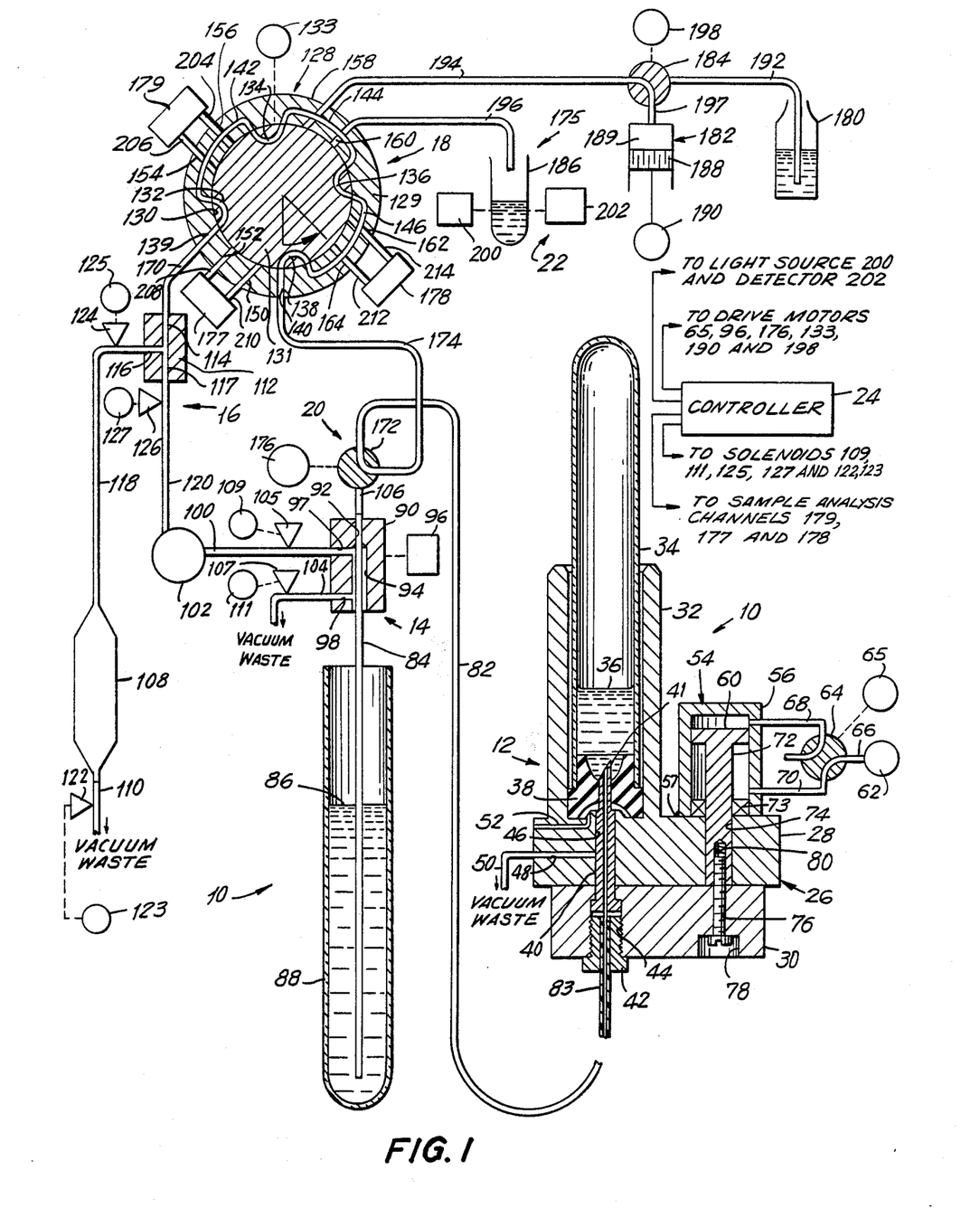
FIG. 1 is an essentially diagrammatic view of a new and improved sampler representatively configured and operable in accordance with the teachings of my invention, as depicted in operable relationship with sample analysis apparatus, and includes certain components depicted in cross-section.
Figure 2:
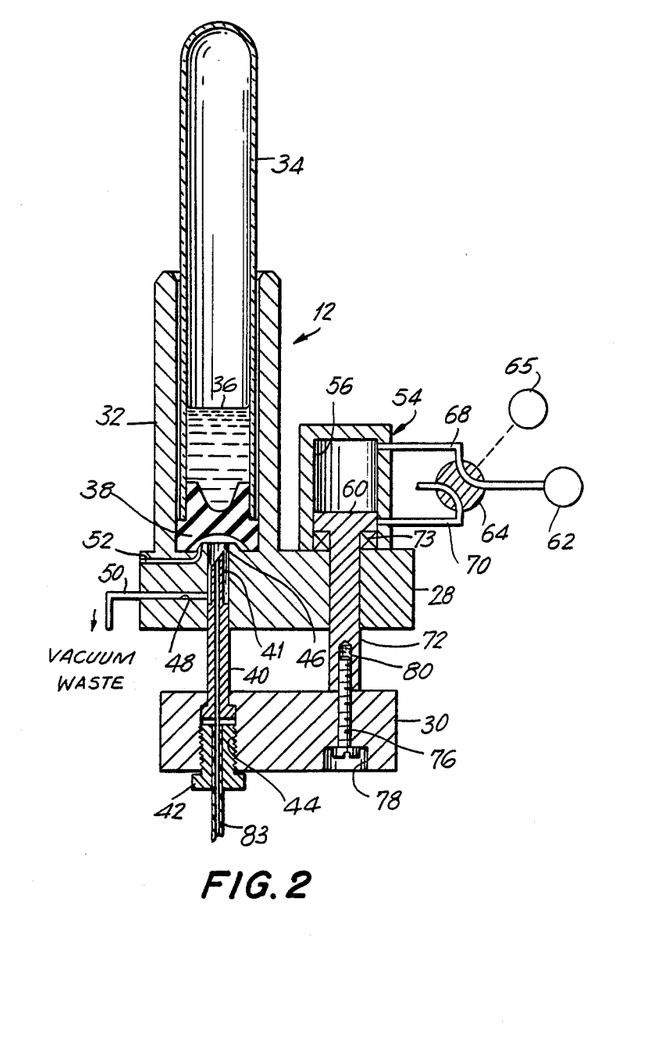
FIG. 2 is an essentialy cross-sectional view of the closed tube sampler of FIG. 1 in a different operational condition.

Referring to FIGS. 1 and 2 of the drawings, a new and improved sampler representatively configured and operable in accordance with the teachings of my invention is indicated generally at 10; and comprises a closed tube sampler as indicated generally at 12, and an open tube sampler as indicated generally at 14. Sample supply and sampler rinse apparatus are indicated generally at 16, and a sample valve is indicated generally at 18; and a selector valve is indicated generally at 20, and is operable to selectively connect the sample supply and sampler rinse apparatus 16 to either of the closed tube sampler 12 or the open tube sampler 14 for sample supply to the sample valve 18, and subsequent rinse of the latter and of the relevant sampler.

Automated sample analysis apparatus are indicated schematically at 22; and are depicted in operable relationship with the sampler 10 for automated analysis of the samples as suppled thereto from sample valve 18.

A controller is schematically depicted at 24, and is operable to control the operation of the indicated sampler and sample analysis apparatus components as described in greater detail hereinbelow.

The closed tube sampler 12 comprises a closed sample tube holding assembly 26 which includes upper and lower, relatively movable plates 28 and 30. Upper plate 28 includes an upstanding, open-ended generally cylindrical sample tube insertion guide 32 for guidance and support of an inverted, closed sample-containing tube 34 therein as shown. For a representative application of the sampler 10 of my invention, sample tube 34 may, for example, take the form of that marketed under the Trademark "Vacutainer" by the Becton-Dickinson Company of East Rutherford, N.J., and will include therein a whole blood sample 36 as aspirated directly thereinto from the arm of a patient and retained therein as shown by a stopper 38 of any appropriately inert and self-sealing material such as a suitable rubber. Tube 34 may be manually inserted into tube insertion guide and support 32, or may be mechanically inserted thereinto by any appropriate tube insertion device, not shown, as well as known and understood by those skilled in this art.

A jacketed sampling needle assembly 40, including a sampling needle 41, is fixedly mounted as shown by screw-threaded mounting collar 42 in stepped and internally threaded bore 44 of lower plate 30, and extends upwardly therefrom through aligned bore 46 in upper plate 28 to establish a fluid-tight seal therebetween, albeit with freedom for relative movement. A bore 48 connects bore 46 via vacuum conduit 50 to waste through a suitable source of vacuum, not shown; while a vent bore 52 of small diameter connects bore 46 to atmosphere. Preferably, bore 46 and thus sampling needle 41 are slightly off-center or eccentric relative to tube insertion guide 32 and thus tube stopper 38 for purposes made clear hereinbelow.

Closed tube holding assembly drive means are indicated generally at 54, and comprise a fluid motor having a cylinder 56 fixedly mounted in any appropriate manner, for example spot welding as indicated at 57, on upper plate 28, and a double-acting piston 60 reciprocable therein by pressurized fluid from source 62 as supplied to opposite faces of piston 60 through four way valve as schematically indicated at 64 via conduits 66, 68 and 70. Four way valve 64 is preferably operated by an electrically conrollable device, for example an electric drive motor as schematically depicted at 65, and is rotatable thereby between the valve positions of FIGS. 1 and 2. A piston rod 72 extends as shown downwardly from piston 60 through sealing means 73 and bore 74 in upper plate 28, and is fixedly secured to lower plate 30 by an attachment screw 76 which extends through stepped bore 78 in the lower plate 30 into threaded bore 80 in the bottom face of piston rod 72.

With closed sample tube holding assembly 26 configured as described, it will be clear that with upper and lower plates 28 and 30 in the abutting or "closed" position thereof of FIG. 1, attendant supply of pressurized fluid from source 62 to cylinder 56 below piston 60 via valve 64 and conduits 66 and 70, sampling needle 40 will be effective to pierce tube stopper 38 and extend into fluid flow communication with sample 36 in closed tube 34 as supported in guide 32. Conversely, with upper and lower plates moved to the separated or "open" position thereof of FIG. 2 through supply of pressurized fluid from source 62 to cylinder 56 above piston 60 via valve 64 and conduits 66 and 68, sampling needle 40 will be withdrawn from stopper 38 and exposed in upper plate bore 46 to vacuum via plate bore 48

A flexible sample supply conduit 82 of any appropriately inert, and preferably transparent, material, for example Teflon, connects jacketed sampling needle 40 via sampling needle connector 83 to selector valve 20.

Open tube sampler 14 comprises an off-take probe 84 which extends as shown into a sample 86 contained in an upstanding open sample tube 88 which is positioned relative thereto as shown in FIG. 1 for withdrawal by aspiration by the probe of a predetermined sample portion therefrom. Tube 88 may be manually presented to probe 84, or may be mechanically presented thereto by any appropriate tube presentation device, not shown, as well known and understood by those skilled in this art. For a representative application of the sampler 10 of my invention, tube 88 may take the form of a "Vacutainer," and sample 86 may again be a whole blood sample as aspirated directly thereinto from the arm of a patient.

A generally cylindrical probe wash sleeve is indicated at 90 and comprises a stepped bore 92 which includes an enlarged bore portion 94 through which probe 84 extends as shown with freedom for relative movement therebetween. A generally fluid-tight seal is formed between probe 84 and the upper portion of bore 92. Wash sleeve 90 further comprises spaced rinse solution and vacuum bores 97 and 98 extending as shown generally transverely thereof into communication with enlarged sleeve bore portion 94. Bore 97 is operable via flexible conduit 100 to supply a pressurized rinse solution from a source 102 thereof to the upper end of bore portion 94; while bore 98 is operable via flexible conduit 104 to connect the lower end of bore portion 94 to waste through a suitable vacuum source, not shown.

Figure 3:
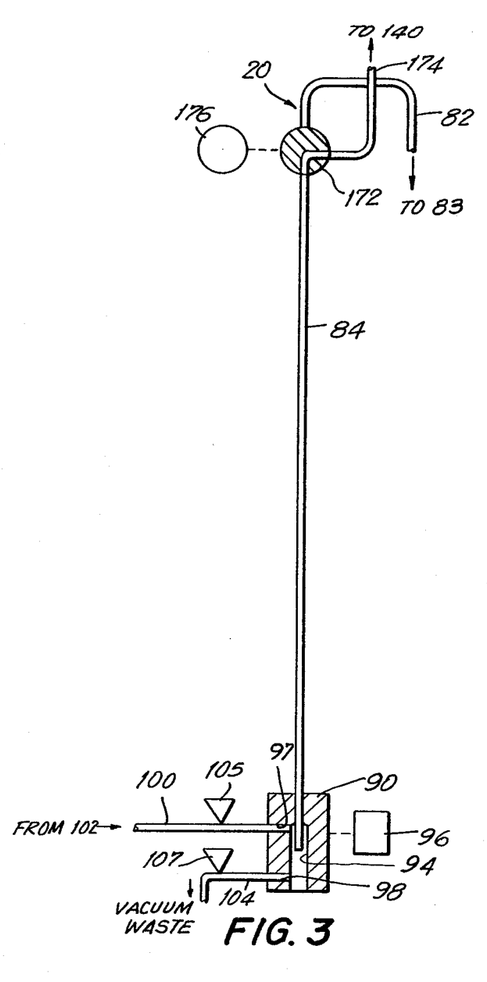
FIG. 3 is an essentially cross-sectional view of the open tube sampler of FIG. 1 in a different operational condition.

Wash sleeve drive means are depicted schematically at 96, and are operatively connected as indicated to wash sleeve 90 to drive the same between the positions thereof of FIGS. 1 and 3 relative to off-take probe 84; upon removal of course of the open tube 88 from the position thereof depicted in FIG. 1. Drive means 96 may, for example, take the form of the electrically controllable fluid motor 54 which forms the closed tube holding assembly drive means; in which instance the motor piston rod would be connected to the wash sleeve 90 to reciprocate the same between the wash sleeve positions of FIGS. 1 and 3.

Valves taking for example the form of suitable pinch valves are schematically indicated at 105 and 107, and are respectively operatively associated with flexible rinse and vacuum conduits 100 and 104 as shown to control fluid flow therethrough. Valves 105 and 107 are preferably operated by electrically controllable devices, for example solenoids, as indicated schematically at 109 and 111.

A flexible sample supply conduit 106 connects off-take probe 84 to selector valve 20.

Sample supply and sampler rinse apparatus 16 comprise a pressure equilibration chamber 108 which is connected via flexible conduit 110 as indicated to waste through a suitable vacuum source, not shown. An electrically operable conductivity detector is schematically depicted at 112, and includes interconnected flow passages 114, 116 and 117 extending therethrough as shown. A flexible conduit 118 connects conductivity detector passage 116 to equilibration chamber 108, and a flexible conduit 120 connects conductivity detector flow passage 117 to pressurized rinse source 102. As well known and understood by those skilled in this art, conductivity detector 112 is operable to detect the presence of sample fluids in passages 114 and 117, on the basis of the resultant conductivity changes thereacross, and to generate and output an electrical signal indicative thereof.

Valves taking the form of pinch valves are schematically depicted at 122, 124 and 126, and are respectively operatively associated as shown with flexible conduits 110, 118 and 120 to control fluid flow therethrough. Valves 122, 124 and 126 are preferably operated by electrically controllable devices, for example solenoids, as schematically depicted at 123, 125 and 127, respectively.

Figure 4:
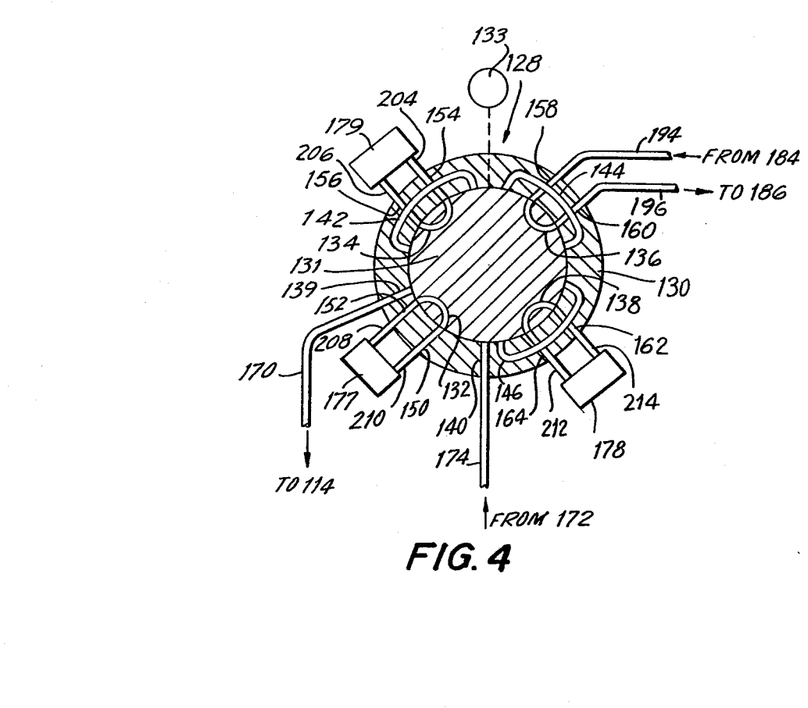
FIG. 4 is an essentially cross-sectional view of the sample valve of FIG. 1 in a different operational condition.

The sample valve 18 takes the form of a shear valve 128 which comprises a stationary, generally cylindrical outer valve body part 129 having a bore 130 formed therein, and a generally cylindrical inner valve body part 131 disposed as shown in generally fluid-tight manner in bore 130 and rotatable relative thereto between the positions thereof of FIGS. 1 and 4 by operatively connected electrically operated drive means preferably taking the form of an electric drive motor as schematically depicted at 133. Inner valve body part 131 comprises spaced sample fluid loops or passages 132, 134, 136 and 138 formed therein as shown; while other valve body part 129 comprises sample fluid passages 139 and 140, and spaced sample fluid loops or passages 142, 144 and 146 which are respectively precisely alignable with inner valve body loops 132, 134, 136 and 138 to form a continuous sample fluid passage extending through the sample valve from outer valve body passages 139 to 140 when the sample valve is in the position thereof as depicted in FIG. 1.

Further included in the outer valve body part 129 of the shear valve 128 are spaced fluid passage pairs 150 and 152, 154 and 156, 158 and 160, and 162 and 164, which are respectively precisely alignable as shown with inner valve body part loops 132, 134, 136 and 138 with inner valve body part 130 rotated to the FIG. 4 position thereof by drive motor 133 to form four discrete sample fluid flow passages extending through the valve, none of which are in fluid flow communication with closed or open tube samplers 12 and 14 or with the sample and sampler rinse supply apparatus 16.

A flexible conduit 170 connects outer valve body passage 139 to flow passage 114 in conductivity detector 112.

Figure 5:
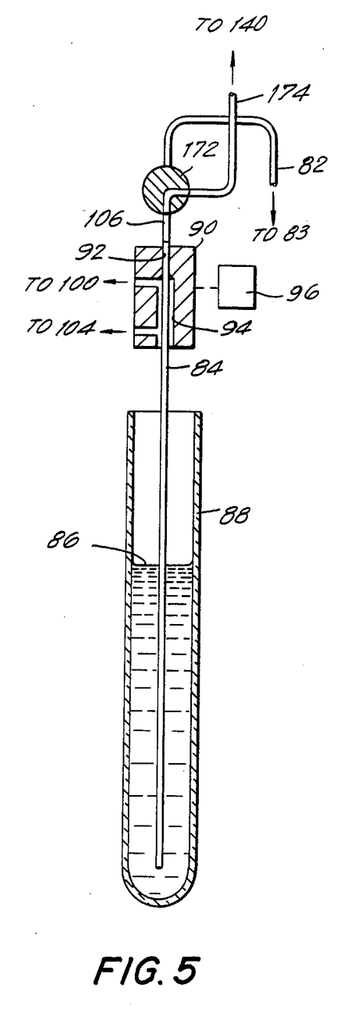
FIG. 5 is an essentially cross-sectional view of the open tube sampler and selector valve of FIG. 1 in different operational conditions.

Selector valve 20 comprises a three way valve as schematically depicted at 172 which is connected as shown by flexible conduit 174 to passage 140 of shear valve 128. Three way valve is rotatable between the positions thereof of FIG. 1 and FIGS. 3 and 5 by operatively connected, electrically operated drive means taking, for example, the form of an electric drive motor as schematically depicted at 176. With the three way valve 172 in the position thereof of FIG. 1, it will be clear that closed tube sampler 10 will be operatively connected therethrough to shear valve 128 via conduits 82 and 174; while open tube sampler 14 will be effectively disconnected and isolated from the sample supply circuit of the sampler apparatus 10. Conversely, with the three way valve 172 in the position thereof of FIG. 5, it will be clear that the open tube sampler 14 will be operatively connected therethrough to shear valve 128 via conduits 106 and 174; while closed tube sampler 12 will be effectively disconnected and isolated from the sample supply circuit of the sampler apparatus 10.

For use with a sample valve 18 taking the form of shear valve 128 which is operable as depicted and described to form four separate and discrete sample loops 132, 134, 136 and 138 with the inner valve body part 131 rotated by drive motor 133 to the position thereof of FIG. 4, it will be clear to those skilled in this art that the sample analysis apparatus 22 may advantageously include four discrete, albeit concomitantly operable, automated sample analysis channels operatively associated with said shear valve on the basis of one of said sample analysis channels for each of said sample loops. One of these sample analysis channels, as indicated generally at 175, is representatively depicted in some detail, albeit schematically, in FIG. 1; while the remaining three of such sample analysis channels are depicted in block diagram form at 176, 177 and 178, all in operative relationship with the shear valve 128.

Figure 6:
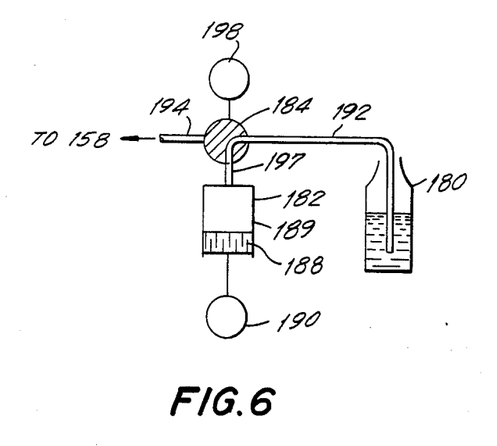
FIG. 6 is an essentially cross-sectional view of the analysis apparatus reagent valve and metering pump of FIG. 1 in different operational conditions.

As schematically depicted in FIG. 1, automated sample analysis channel 175 comprises a reagent(s) source 180, a reagent metering pump 182, a three way reagent valve 184, and a sample-reagent reaction and analysis chamber 186. Reagent metering pump 182 comprises a piston 188 which is reciprocable in a cylinder 189 by an electric drive motor 190. A flexible conduit 192 connects reagent(s) source 180 to reagent valve 184; while flexible conduits 194 and 196 respectively connect reagent valve 184 and reaction and analysis chamber 186 to passages 158 and 160 in shear valve 128, thus effectively connecting sample analysis apparatus channel 175 to shear valve sample loop 136 when the shear valve 128 is in the FIG. 4 position thereof. A flexible conduit 197 connects reagent metering pump 182 to three way valve 184; while electrically controllable drive means, preferably taking the form of an electric drive motor as depicted schematically at 198 are operatively connected as indicated to reagent valve 184 and are operable to rotate the same between the positions thereof of FIG. 1 and FIG. 6 to either connect reagent pump 182 to source 180 or to the shear valve 128. Further included in automated sample analysis channel 175 are sample analysis means taking, for example, the form of a light source 200, such as a laser, and a light-sensitive detector 202, respectively operatively associated with sample-reagent reaction and analysis chamber 186 and operable to automatically analyze reacted samples contained therein in manner(s) well known and understood by those skilled in this art.

Flexible conduits 204 and 206, 208 and 210, and 212 and 214, are provided to respectively connect sample analysis apparatus channels 176, 177 and 178 as shown to shear valve sample loops 134, 132 and 138 when the inner valve body part 131 is rotated to the position thereof of FIG. 4; and it will be clear that the respective sample analysis apparatus channels 176, 177 and 178 may take any of a wide variety of configurations compatible with automated sample analysis.

Controller 24 may, for example, take the form of an appropriately programmable microprocessor device which is operable as indicated through non-illustrated power supply devices to electrically control, i.e. start, stop, sequence and time, the respective operations of the sampler and sample analysis apparatus components as indicated on FIG. 1 of the drawings.

For operation of the sampler 10 of my invention to supply a sample from closed tube sampler 12 to sample analysis apparatus 22, and with no tube 34 initially in place in tube insertion and support guide 32, it will be understood that controller 24 would be activated to open pinch valve 124, close pinch valves 122, 126, 105 and 107, and position shear valve 128, three way valve 172 and four way valve 64 as depcited in FIG. 1. This effectively isolates open tube sampler 14 from the sampler 10, and brings tube holding assembly 26 to the "closed" position thereof of FIG. 1; and insures ambient atmospheric pressure in equilibration chamber 108 via the open and exposed tip of sampling needle 41 through the relevant connected conduits and fluid passages. Concomitantly, controller 24 operates to drive reagent valve 184 to the FIG. 6 position thereof, and to drive reagent metering pump piston 188 downwardly as shown to bottom dead center to aspirate reagent(s) from source 180 via conduit 193 and charge pump cylinder 189 therewith.

Closed sample tube 34 with stopper 38 firmly in place is then manually inserted into tube insertion guide 32 and forced downwardly until the stopper abuts and comes to rest at the upper surface of plate 28. This results in needle 41 piercing stopper 38 and extending as shown into fluid flow communication with sample 36. Under these circumstances, it will be clear that vacuum build-up in closed tube 34 above sample 36, as might otherwise develop attendant repetitive sample aspiration from the same closed sample tube, will be advantageously eliminated by the flow of the necessary quantity of air at ambient atmospheric pressure from the equilibration chamber 108 to the interior of closed tube 34 above the sample 36 via the open end of needle 41; it being understood by those skilled in this art that vacuum build-up of the nature under discussion in closed tube 34 could very well result in the formation and inclusion of micro-bubbles in sample(s) as aspirated therefrom with attendant reduction in the overall quantity of sample available for analysis, and significant and contemporarily unacceptable degradation in sample analysis accuracy. The problem of micro-bubble formation in aspirated sample(s) is of particular concern in contemporary sample analysis apparatus wherein increasingly small quantities, for example 100 micro-liters, of sample are aspirated for supply to sample analysis apparatus, and wherein the accuracy of the sample analysis results are closely predicated upon the availability in each instance of a precisely known sample quantity for analysis; in this instance the respective sample quantities as contained in shear valve loops 132, 134, 136 and 138 as described in detail hereinbelow. Too, in those instances wherein closed tube 34 is constituted by a "Vacutainer," and wherein a short "pull" from a patient results insignificantly less than an optimal quantity of blood sample available therein for analysis, it will be clear to those skilled in this art that the addition of air at ambient atmospheric pressure to closed tube 34 as described above sample 36 may prove essential as a practical matter to permit satisfactory sample aspiration therefrom.

Following pressure equilibration as above between equilibration chamber 108 and closed sample tube 34—this in reality is accomplished almost instantaneously upon the entry of sampling needle into the closed tube—controller 24 operates to open pinch valve 122, thus connecting the relevant vacuum source through conduit 110 to sampling needle 41, whereby sample 36 will be aspirated from closed tube 34 via needle 41, connector 83, conduit 82, valve 172 and conduit 174 to flow into and through and fill connected shear valve passages and loops 140, 138, 146, 136, 144, 134, 142, 132 and 139, and to flow from the latter via conduit 170 into passage 114 of conductivity detector 112. Upon the arrival and detection of the leading edge of the thusly aspirated sample in the conductivity detector 112, the latter will operate to signal controller 24 to close pinch valve 124 to discontinue sample aspiration from closed tube 34.

Controller 24 then operates to rotate the inner body part 131 of shear valve 128 to the FIG. 4 position thereof, thus effectively shearing the sample-filled flow passage through valve 128 into four discrete, and precisely volumetrically determined, sample segments as respectively contained in shear valve loops 136, 134, 132 and 138 which are now respectively placed in fluid flow communication with sample analysis apparatus channels 175, 176, 177 and 178 via valve passages 158 and 160 and conduits 194 and 196, valve passages 154 and 156 and conduits 204 and 206, valve passages 152 and 150 and conduits 208 and 210, and valve passages 164 and 162 and conduits 212 and 214.

For sample analysis by sample analysis apparatus channel 175, controller 24 then operates to return reagent valve 184 to the FIG. 1 position thereof and to drive reagent metering pump piston 188 to top dead center to pump a precisely metered reagent quantity into conduit 194 through valve 184, thus inserting the sample contained in shear valve loop 136 into the reagent flow path formed by conduit 194, valve passage 158, loop 136, valve passage 160 and conduit 196, and flushing the resultant sample-reagent solution into reaction and analysis chamber 186 for thorough sample-reagent mixing and reaction, and automated sample analysis attendant subsequent activation by controller 24 of light energy source 200 and detector 202. Controller 24 then returns reagent valve 184 to the FIG. 6 position thereof for re-charging as described of reagent pump 182 with reagent from source 180.

Sample analysis apparatus channels 176, 177 and 178, which may be of the same or different configurations than analysis channel 175, are concomitantly operated by controller 24 to acquire, react (if required), and analyze the respective sample quantities from shear valve loops 134, 132 and 138.

Controller 24 then operates to return shear valve 128 to the FIG. 1 position thereof thus re-establishing the continuous flow path therethrough; and to rotate four way valve 64 to the FIG. 2 position thereof, thereby operating fluid motor 54 to drive the closed tube holding assembly 26 to the "open" position thereof of FIG. 2. This retracts the tip of sampling needle 41 into bore 46 in upper plate 28, thereby exposing the same to vacuum via the now uncovered vacuum bore 48 and conduit 50.

Particularly thorough rinsing and cleansing of the sample-contaminated flow path from the open tip of needle 41 to and through the shear valve 128 to minimize sample carryover, e.g. the contamination of a succeeding sample by the residue of a preceding sample, and maximize the accuracy of subsequent sample analysis, is then initiated by the re-opening of pinch valve 124 via controller 24 to re-connect the sampling needle 41 to the relevant vacuum source and thereby aspirate the vast bulk of the sample remaining in needle 41, connector 83, conduit 82, three way valve 172, conduit 174, shear valve passages and loops 140, 138, 146, 136, 144, 134, 142, 132 and 139, conduit 170, and conductivity detector passage 114 to waste through conductivity detector passage 116, conduit 118, equilibration chamber 108 and conduit 110, respectively. Of course, the atmospheric air required by this aspiration of remaining sample to waste is provided by vent bore 52 in the upper plate 28 of the closed tube holding assembly 26. Controller 24 then operates to close pinch valve 124 and open pinch valve 126, thereby providing for the forceful flow of pressurized rinse solution from source 102, through conduit 120, conductivity detector passages 117 and 114, conduit 170, the above-specified connected shear valve passages and loops, conduit 174, three way valve 172, conduit 82, connector 83 and jacketed sampling needle 40, respectively, to waste via bore 46, vacuum bore 48 and conduit 50. This results in the particularly effective and thorough rinsing and cleansing, by forceful rinse solution back flushing as described, of the entire sample sample supply path from the tip of sampling needle 41 to and through the shear valve 128; and, in addition, results in like manner in the particularly thorough rinsing and cleansing of the exposed outer surface of the tip of sampling needle 41 as the rinse solution flows from the open needle tip downwardly and completely around that surface on its way to vacuum bore 48.

Controller 24 then operates to re-close pinch valve 126 and re-open pinch valve 124, thereby discontinuing pressurized rinse solution supply, evacuating the rinse solution from the entire sample supply path of interest to waste via conduit 110, and subsequently effectively air-drying that entire sample supply path and the exposed outer surface of the sampling needle tip. Thus, all relevant sampler and valve components are left essentially clean and dry, sample carryover with regard to a succeeding sample reduced to an absolute and clinically insignificant minimum, and the accuracy of succeeding sample analysis results maximized.

Closed sample tube 34 is manually removed from tube insertion and support guide 32 on the tube holding assembly 26 at or before the completion of the rinsing and drying operation.

At the completion of the rinsing and drying operation, controller operates to re-close pinch valve 122 and return four way valve 64 to the FIG. 1 position thereof, thus again effectively insuring ambient atmospheric pressure in the equilibration chamber 108, and returning the closed tube holding assembly 26 to the "closed" position thereof of FIG. 1 in readiness for repetition of the closed tube sampling and analysis cycle as described.

Sampling needle 41 is disposed somewhat off-center vis-a-vis closed tube insertion and support guide 32 to reduce from virtual certainty the probability attendant subsequent re-introduction of the same closed sample tube 34 to closed tube sampler 12 that needle 41 will pierce the tube stopper 38 at precisely the same location, thereby unduly weakening the latter and introducing the unacceptable possiblity of leakage at the point where the needle pierces the stopper.

For operation of the sampler 10 of my invention to supply a sample from open tube sampler 14 to sample analysis apparatus 22 for analysis, and with a sample-containing open tube 88 presented as depicted in FIG. 1 to immerse off-take probe 84 in the sample 86, and wash sleeve 90 positioned as in FIG. 1, it will be understood that controller 24 would be activated to close pinch valves 105, 126 and 107, open pinch valves 124 and 122, and position three way valve 172 and shear valve 128 as in FIG. 1. This effectively isolates closed tube sampler 12 from the sampler 10, and results in the aspiration and flow under the influence of the relevant vacuum source of the sample 86 from open tube 88 via the open end of off-take probe 84, conduit 106, three way valve 172, conduit 174, the above-specified connected passages and loops of shear valve 128, and conduit 170, into passage 114 of the conductivity detector 112, respectively, thus again resulting in the filling of the shear valve sample loops 138, 136, 134 and 132 with sample. Concomitantly, controller 24 would operate sample analysis channel 175 to charge reagent metering pump 182 with reagent(s) as described hereinabove.

Upon detection of the leading edge of sample 86 in conductivity detector passage 114, the detector will signal controller 24 to close pinch valve 124, thus discontinuing further sample aspiration from open tube 88, and to rotate shear valve 128 to the FIG. 4 position thereof. Sample analysis channels 175, 176, 177 and 178 are then operated by controller 24 to acquire, react (if required in all instances), and automatically analyze the respective sample quantities from shear valve loops 136, 132, 134 and 138, all as described in some detail hereinabove with regard to the operation of the closed tube sampler 12; and open sample tube 88 is removed from registration with the off-take probe 84.

Following sample quantity acquisition as described by analysis apparatus 22, controller 24 operates to rotate shear valve 128 back to the FIG. 1 position thereof, thus re-establishing the continuous flow path therethrough, and to re-open pinch valve 124 to aspirate to waste most of the sample 86 remaining in the probe 84, conduit 106, selector valve 172, conduit 174, and the re-connected shear valve passages and loops, respectively, through conduit 170, detector passages 114 and 116, conduit 118, chamber 108 and conduit 110. Concomitantly, controller 24 operates to open pinch valves 105 and 107, thus forcefully introducing the pressurized rinse solution from source 102 via conduit 100 and wash sleeve bore 97 at the top of wash sleeve bore portion 94 to surround and forcefully contact the outer surface of the off-take probe 84, and withdrawing the thusly introduced rinse solution from the bottom of wash sleeve bore portion 94 to waste through sleeve vacuum bore 98 and conduit 104. Controller 24 now also operates to actuate wash sleeve drive motor 96 to drive the thusly operating wash sleeve from the FIG. 1 to FIG. 3 position thereof, thus effectively causing the operating wash sleeve to traverse substantially the entire outer surface of the off-take probe 84 thereby thoroughly rinsing the same and removing therefrom the residue of the sample 86 therefrom.

As the wash sleeve 90 reaches the FIG. 3 position thereof, it will be understood that the vacuum existing in the tip portion of probe 84 will operate to aspirate the rinse solution from wash sleeve rinse solution bore 97, as mixed of necessity with some measure of ambient atmospheric air, into the open probe tip for flow following the remaining sample as described to waste via conduit 110. As well understood by those skilled in this art, this flowing mixure of air, in the form of air bubbles, and the rinse solution, will have a particularly effective cleansing action on the interior of probe 84, conduit 106, selector valve 172, conduit 104, and the relevant connected passages and loops of shear valve 128 with regard to the particularly thorough removal of the residue of sample 86 therefrom.

Controller 24 then operates to close pinch valves 105 and 124, and to open pinch valve 126, thereby discontinuing rinse solution supply to the wash sleve 90, and commencing rinse solution supply to probe 84 via conduit 120, detector passages 117 and 114, conduit 170, the relevant connected passages and loops of shear valve 128, conduit 174, selector valve 172, conduit 106 and probe 84, thereby backflushing the same with rinse solution against the direction of sample flow therein for additional, particularly thorough and effective cleansing thereof with regard to the residue of sample 86. As this backflushing rinse solution exits the tip of probe 84, the same is simply aspirated to waste via wash sleeve vacuum bore 98 and conduit 104, thus preventing contaminated rinse solution spillage at the situs of operation of sampler 10. Of particular significance with regard to probe backflushing in instances wherein the sample(s) of interest are constituted by whole blood samples is the demonstrated effectiveness of the same with regard to removal of otherwise difficult-to-remove fibrinogen, or clotted blood fibrin materials.

At the completion of probe and sample supply means backflushing as described, controller 24 operates to close pinch valve 126 and open pinch valve 124 to aspirate the rinse solution remaining in the probe 84, conduit 106, selector valve 172, conduit 174, the relevant connected passages and loops of shear valve 128, to waste via conduit 170, detector passages 114 and 116, conduit 118, chamber 108 and conduit 110, respectively, thus effectively again flushing the same with rinse solution in the direction of sample flow to complete the particularly thorough cleansing thereof with rinse solution vis-a-vis the residue of sample 86. Ambient atmospheric air will, of course, be aspirated into probe 84 following aspiration of the remaining rinse solution therefrom as described to waste to air-dry the same, and all other relevant sampler components, to complete the cleansing thereof. Concomitantly, controller 24 operates to actuate wash sleeve drive motor 96 to return the wash sleeve 90 to the FIG. 1 position thereof, thus effectively air-drying the same due to the flow of ambient atmospheric air around the probe into wash sleeve vacuum bore 98, to thus complete the cleansing of the probe exterior.

At the completion of the above, controller 24 operates to re-close pinch valves 122 and 107 to prepare open tube sampler 14 for a succeeding cycle of operation as described upon presentation of another open sample-containing tube to the off-take probe 84 as described.

Although the closed tube sampler 12 of my invention has been heretofore representatively illustrated and described as operable through the generally vertical orientation of the sampling needle 41 below the closed sample-containing tube 34, it may be understood that the closed tube sampler 12 is also operable with the sampling needle 41 oriented differently, and nor necessarily "below" the closed sample-containing tube 34.

Figures 7, 8:
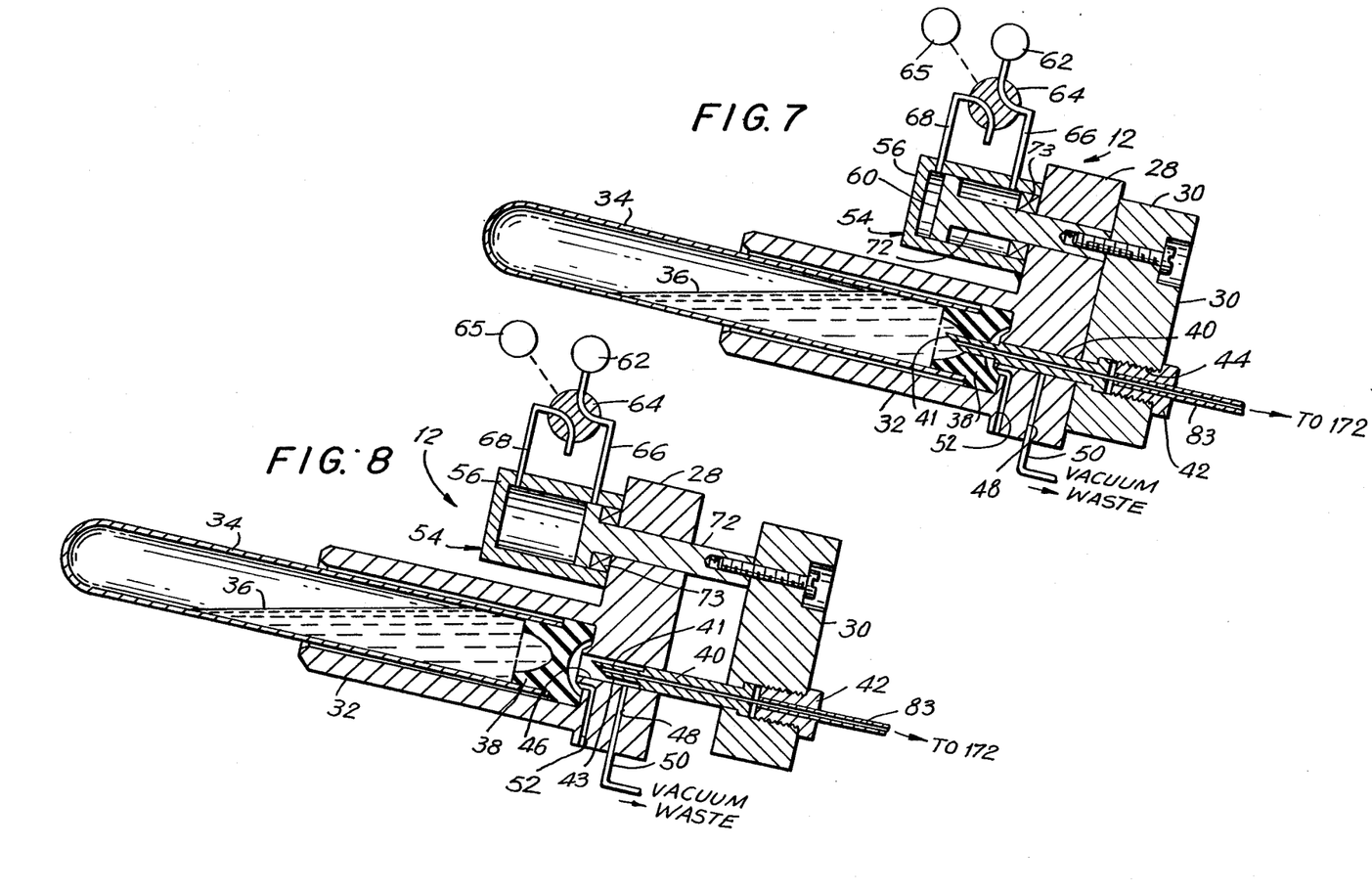
FIG. 7 is an essentially cross-sectional view of the closed tube sampler of FIGS. 1 and 2 in a different operational orientation.
FIG. 8 is an essentially cross-sectional view of the closed tube sampler of FIG. 7 in a different operational condition.

More specifically, FIGS. 7 and 8 illustrate a representative application of the closed tube sampler 12 wherein the sampling needle 41 is somewhat slanted as shown relative to the horizontal at, for example, an angle of approximately 18°; with the closed sample-containing tube 34 again of course oriented in alignment therewith by the closed tube insertion and support guide 32. FIG. 7 depicts the closed tube sampler 12 in the "closed" position thereof relative to closed tube 34 as depicted and described in detail hereinabove with regard to FIG. 1 wherein the sampling needle 41 has pierced the tube stopper 38 and entered the sample 36 for aspiration therefrom; while FIG. 8 depicts the closed tube sampler 12 in the "open" position thereof as depicted and described in detail hereinabove with regard to FIG. 2 wherein sample aspiration has been completed, and the sampling needle withdrawn from closed tube stopper 38 and is in the process of being thoroughly rinsed.

To again insure absolute thoroughness of this rinse of the sampling needle 41, in particular with regard to the thorough rinsing and cleansing of the exposed outer surface of the sampling needle tip portion as seen at 43 in FIG. 8, it will be understood that the flow rate of ambient air through vent 42 into and around that entire exposed outer needle tip portion surface in the annulus formed between the same and the bore 46 in upper plate 28, and therefrom through vacuum bore 48 in that plate and the connected vacuum conduit 50 to waste, is predetermined to be significantly greater than the flow rate of the back flushing rinse solution which flows as heretofore described from the open tip of sampling needle 41 into that annulus upon back flushing of the sampling needle. This is, as a practical matter, readily accomplishable due to the very small flow area provided by the bore in sampling needle 41 which, for a representative application of the method and apparatus of my invention, may have a diameter as small as $\frac{1}{2}$ mm.

In accordance with the above, it will be clear that, as the back-flushing rinse solution from pressurized source 102 (FIG. 1) flows from the open tip of sampling needle 41, the rinse solution will be immediately mixed with and re-directed by the signifcantly greater volume of ambient air flowing past and around the sampling needle tip opening in generally swirling fashion in the needle tip-upper plate bore annulus; with the overall and particularly beneficial result being that a very effective—in terms of scrubbing action—mixture of the ambient air and the rinse solution will forcefully flow around the entire exposed tip portion of the sampling needle 41 in the needle tip-upper plate annulus to very thoroughly cleanse that exposed sampling needle tip portion; and will subsequently flow directly therefrom to waste through vacuum bore 48 and vacuum conduit 50. Thus, absolute minimization of sample liquid carryover with regard to both the exterior and interior of the sampling needle 41 is again provided, despite the fact that the sampling needle is oriented differently than as depicted in FIGS. 1 and 2.

Figure 9:
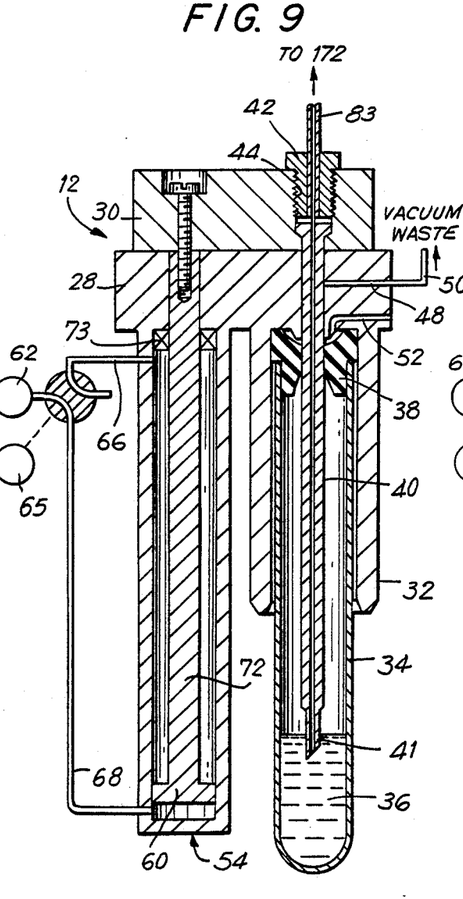
FIG. 9 is an essentially cross-sectional view of a closed tube sampler which is structurally very similar to the closed tube sampler of FIGS. 1 and 2, and depicts the same in a different operational orienation.
Figure 10:
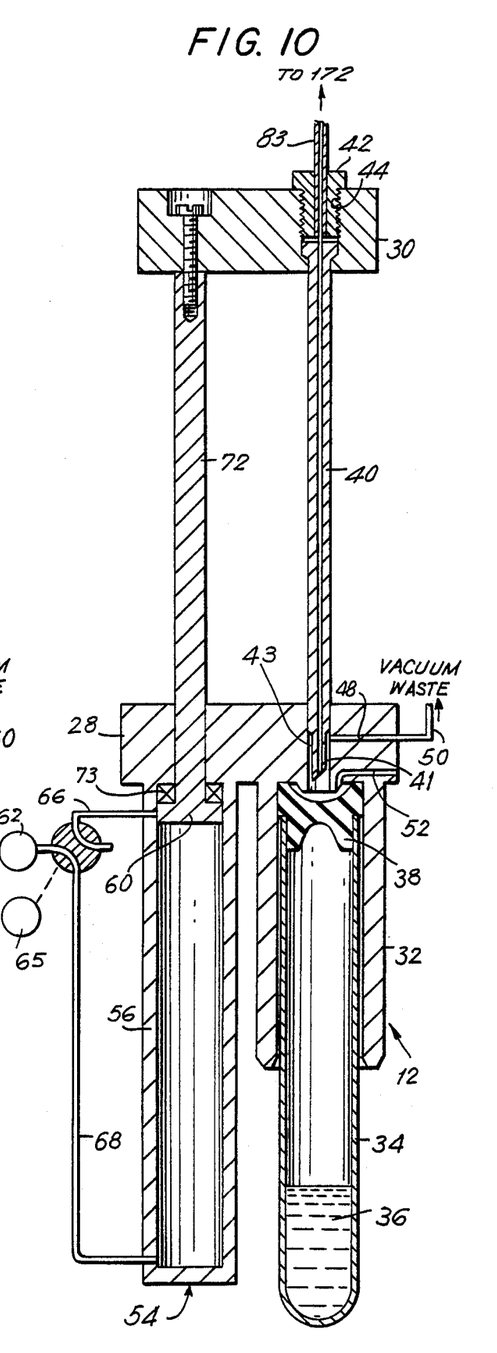
FIG. 10 is an essentially cross-sectional view of the closed tube sampler of FIG. 9 in a different operational condition.

FIGS. 9 and 10 illustrate another representative application of the closed tube sampler 12 wherein the sampling needle 41, although again generally vertically oriented, faces downwardly and is disposed as shown above rather than below the sample-containing closed tube 34, which is again of course oriented in alignment therewith by the closed tube insertion and support guide 32. FIG. 9 depicts the closed tube sampler 12 in the "closed" position thereof relative to closed tube 34 as depicted and described in detail hereinabove with regard to FIG. 1 wherein the sampling needle 41 has pierced the tube stopper 38 and entered the sample 36 for aspiration therefrom; while FIG. 10 depicts the closed tube sampler 12 in the "open" position thereof as depicted and described in detail hereinabove with regard to FIG. 2 wherein sample aspiration has been completed, and the sampling needle 41 retracted from the closed stopper 38 into the bore 46 in the upper plate 28 and is in the process of being thoroughly rinsed. Of course, utilization of the closed tube sampler 12 oriented as depicted in FIGS. 9 and 10 requires the depicted increases in the respective lengths of the sampling needle 41, and the cylinder 56 and piston rod 72 of the closed tube holding assembly drive motor means 54; thus insuring that the sampling needle 41 is of sufficient extent to reach a sample 36 in the bottom portion of closed tube 34, and that the stroke of the fluid motor drive means 54 is of correspondingly sufficient extent to move the sampling needle 41 between the FIG. 9 and 10 positions thereof.

With the closed tube sampler oriented as depicted in FIGS. 9 and 10, and with the sampling needle in the retracted position thereof in the needle tip-plate bore annulus for rinsing as depicted in FIG. 10, it will be clear that predetermination as heretofore described of the flow rate of ambient air through vent 52 into that annulus to be significantly greater than the flow rate of the back flushing rinse solution from the open tip of sampling needle 41 will again result in the immediate mixture of redirection of that rinse solution with and by that flowing ambient air in the needle tip-plate bore annulus, to again very thoroughly scrub and cleanse the entire exposed tip portion of the sampling needle 41 as the thusly mixed rinse solution and ambient air forcefully flow completely around that needle tip portion in the annulus, and therefrom to waste through vacuum bore 48 and vacuum conduit 50. This makes clear that absolute minimization of sample liquid carryover is again provided with regard to both the exterior and interior of the sampling needle 41, despite the fact that, in FIGS. 9 and 10, the sampling needle 41 is oriented in exactly the opposite manner as that shown in FIGS. 1 and 2.

By the above is believed made clear that the closed tube sampler 12 can be operably oriented in any desired manner throughout the available 360° range of such orientations, without sacrifice of any nature in the sample liquid carryover minimization effectiveness of the apparatus and method of my invention, in particular to the critical very thorough cleansing of the exposed exterior portion of the sampling needle 41 following closed tube sample aspiration.

Of course, this capability for effective closed tube sampler operation in any desired orientation adds significantly to the versatility of application of the apparatus and method of my invention.

Although disclosed hereinabove as stationary relative to upper closed tube holding assembly plate 28, it will be clear that tube insertion and support guide 32 may be movable relative thereto taking, for example, the form of a plurality of such tube insertion and support guides as may be disposed in a manner well understood by those skilled in this art on a turntable or like device and which are indexable in turn into the depicted operational position for sampling in turn from the closed sample-containing tubes as inserted and supported therein.

Although disclosed hereinabove by way of representative example as applied to the sampling and analysis of blood samples, it will be clear to those skilled in this art that the apparatus and method of my invention are by no means limited to use with samples as constituted by blood.

Various changes may, of course, be made in the hereindisclosed preferred embodiment of my invention without departing from the spirit and scope thereof as defined by the appended claims.

What is claimed is:

1. In sampler apparatus which include sample supply means to supply samples from a closed sample container by introducing operatively connected sample aspiration means thereinto, and means to remove said sample aspiration means from said closed sample container following sample aspiration, the improvements comprising, rinse means operatively connected to said sample supply means and operable upon the removal of said sample aspiration means from said closed sample container following sample aspiration therefrom to flow a rinse through said sample supply means and said sample aspiration means against the direction of aspirated sample flow therethrough, said sample supply means being further operable to then flow said rinse therefrom and from said sample aspiration means in the direction of aspirated sample flow therethrough, whereby said sample supply means and said sample aspiration means will be backflushed by said rinse against the direction of aspirated sample flow therethrough to remove aspirated sample residue therefrom, and will be flushed by said rinse in the direction of aspirated sample flow therethrough to further remove aspirated sample residue therefrom, respectively.

2. In sampler apparatus as in claim 1 further comprising, sample aspiration and supply means to supply samples from an open sample container by introducing sample aspiration means thereto, and selector means operatively associated with said closed and open sample container sample supply means and operable to select therebetween for sample supply from said sampler apparatus.

3. In sampler apparatus as in claim 2 wherein, said rinse means are operatively connectable by said selector means to said open sample container sample supply and sample aspiration means, said rinse means being operable upon such connection following sample aspiration from said open sample container to flow a rinse through said open sample container sample supply and sample aspiration means against the direction of aspirated sample flow therethrough, thereby backflushing said open sample container sample supply and sample aspiration means to remove aspirated sample residue therefrom.

4. In sampler apparatus as in claim 3 wherein, said sample supply means are further operable to flow said rinse therefrom and from said open sample container sample aspiration means in the direction of aspirated sample flow therethrough, thereby flushing said sample supply and open sample container sample aspiration means to remove aspirated sample residue therefrom.

5. In sampler apparatus as in claim 3 wherein, said open sample container sample aspiration means comprise a probe, and wherein said rinse means further comprise means operatively associated with said probe and operable to rinse the exterior thereof to remove aspirated sample residue therefrom.

6. In sampler apparatus which include sample supply means to supply samples from a closed sample container by introducing operatively connected sample aspiration means thereinto, and means to remove said sample aspiration means from said closed sample container following sample aspiration, the improvements comprising, rinse means operatively connected to said sample supply means and operable upon the removal of said sample aspiration means from said closed sample container following sample aspiration therefrom to flow a rinse through said sample supply means and said sample aspiration means against the direction of aspirated sample flow therethrough thereby backflushing said sample supply means and said sample aspiration means to remove aspirated sample residue therefrom, said sample aspiration means comprising a generally vertically oriented sampling needle having a sample aspirating opening at the upper portion thereof, and wherein said rinse means are operable to flow said rinse through the interior of said sampling needle and out of said sampling needle opening for free downward flow around the exterior of said sampling needle to thereby remove aspirated sample residue from both the interior and exterior of said sampling needle.

7. In sampler apparatus as in claim 6 wherein, said closed sampler container is generally vertically oriented above said sampling needle and comprises a stopper closing the bottom end of the same, and wherein said sampling needle is operable to pierce said stopper for sample aspiration from said container.

8. In sampler apparatus as in claim 7 wherein, said stopper is generally circular, and said sampling needle is disposed off-center relative to said stopper whereby, said sampling needle will not pierce the center of said stopper attendant sample aspiration from said container.

9. In a method for supplying a sample from a closed sample container by the introduction of sample aspiration means thereinto to withdraw said sample therefrom, and subsequently removing said sample aspiration means from said closed sample container, the steps of, flowing a rinse through said sample aspiration means against the direction of aspirated sample flow therethrough, and subsequently flowing said rinse through said sample aspiration means in the direction of aspirated sample flow therethrough, whereby said sample aspiration means will be backflushed by said rinse to remove aspirated sample residue therefrom, and will be subsequently flushed by said rinse to further remove aspirated sample residue therefrom, said sample aspiration means comprising a generally vertically oriented sampling needle having a sample aspirating opening at the upper portion thereof, said step of backflushing said sample aspiration means with said rinse further comprising, the steps of, flowing said rinse through the interior of said sampling needle and out of said sampling needle opening for free downward flow of said rinse around the exterior of said sampling needle to thereby remove aspirated sample residue from both the interior and exterior of said sampling needle.

10. In a method as in claim 9 further comprising, the steps of, subsequently flowing ambient atmospheric air through said sample aspiration means, thereby air-drying the same to complete the cleansing thereof.

11. In a method for supplying a sample from a closed sample container by the introduction of a sampling needle thereinto to aspirate sample therefrom, and the subsequent removal of said sampling needle from said closed sample container, said sampling needle comprising a sample aspirating opening in the tip portion thereof, the improvements comprising, the steps of, flowing a rinse through said sampling needle and out of said sampling needle opening against the direction of aspirated sample flow therethrough upon the removal of said sampling needle from said closed sampling container to back flush said sampling needle and remove aspirated sample residue from the interior of said sampling needle, and flowing said rinse from said sampling needle opening around the exterior of said sampling needle tip portion to remove sample residue therefrom.

12. In a method as in claim 11, the improvements further comprising, the flow of said rinse around said sampling needle tip portion comprising, the steps of, flowing a fluid from without said sampling needle around said sampling needle tip portion to mix with and direct the flow of said rinse from said sampling needle opening around said sampling needle tip portion.

13. In a method as in claim 12, the improvements further comprising, the flow of said fluid comprising, the steps of, flowing ambient air around said samping needle tip portion.

14. In apparatus for supplying a sample from a closed sample container by the introduction of a sampling needle thereinto to aspirate sample therefrom, and the subsequent removal of said sampling needle from said closed sample container, said sampling needle comprising a sample aspirating opening in the tip portion thereof, the improvements comprising, means operatively associated with said sampling needle for flowing a rinse through said samping needle and out of said sampling needle opening against the direction of aspirated sample flow therethrough upon the removal of said sampling needle from said closed sample container to back flush said sampling needle and remove aspirated sample residue from the interior of said sampling needle, and means operatively associated with said sampling needle for flowing said rinse from said sampling needle opening around the exterior of said sampling needle tip portion to remove sample residue therefrom.

15. In apparatus as in claim 14, the improvements further comprising, said means for flowing said rinse around the exterior of said sampling needle tip portion comprising, means for flowing a fluid from without said sampling needle around said sampling needle tip portion to mix with and direct the flow of said rinse from said sampling needle opening around said sampling needle tip portion.

16. In apparatus as in claim 15, the improvements further comprising, said means for flowing said rinse around the exterior of said sampling needle tip portion further comprising, means operatively associated with said sampling needle tip portion for forming an annulus therewith to surround said sampling needle tip portion for the flow of said fluid and said rinse through said annulus around said sampling needle tip portion.

17. In apparatus as in claim 15, the improvements further comprising, said means for flowing said fluid around said sampling needle tip portion comprising, means for flowing ambient air around said sampling needle tip portion.

* * * * *